United States Patent [19]

Esmon et al.

[11] Patent Number: 5,248,596
[45] Date of Patent: Sep. 28, 1993

[54] METHOD OF DETECTING PROTEOLYTICALLY MODIFIED ANTITHROMBIN

[75] Inventors: Pamela C. Esmon, Richmond; Emma Yee, Albany, both of Calif.; Robert E. Jordan, Malvern, Pa.; Richard M. Nelson, La Jolla, Calif.

[73] Assignee: Miles Inc., Berkeley, Calif.

[21] Appl. No.: 844,354

[22] Filed: Mar. 2, 1992

Related U.S. Application Data

[63] Continuation-in-part of Ser. No. 381,547, Jul. 18, 1989, abandoned, which is a continuation-in-part of Ser. No. 18,548, Feb. 25, 1987, abandoned.

[51] Int. Cl.⁵ .......................................... G01N 33/53
[52] U.S. Cl. ..................... 435/7.92; 435/13; 435/962; 435/967; 435/7.94
[58] Field of Search ............... 435/7.92, 7.94, 962, 435/967, 13; 436/174, 825

[56] References Cited

U.S. PATENT DOCUMENTS

| | | | |
|---|---|---|---|
| 4,517,294 | 5/1985 | Bock et al. | 435/70 |
| 4,632,901 | 12/1986 | Valkirs et al. | 435/5 |
| 4,632,981 | 12/1986 | Bock et al. | 530/393 |
| 5,057,414 | 10/1991 | Stief et al. | 435/13 |

FOREIGN PATENT DOCUMENTS 896543 8/1983 Belgium .

OTHER PUBLICATIONS

Jordan et al, Science 237:777-779 (14 Aug. 1987).
Jordan et al, J. Biol. Chem., 264(18):10493-10500 (Jun. 25, 1989).
Gettins et al, Biochemistry, 27:3634-3639 (1988).
M. Jochum, *Clotting and Other Plasma Factors in Experimental Endotoxemia: Inhibition of Degradation by Exogenous Proteinase Inhibitors*, Eur. Surg Res. 13:152-168 (1981).
M. Jochum, *Effect of Human Granulocytic Elastase on Isolated Human Antithrombin III*, Hoppe-Syler's Z. Physiol. Chem. Bd. 362, S.103-112 (1981).
R. Carrell, *Plakalbumin, $a_1$-antitrypsin, antithrombin and the mechanism of inflammatory thrombosis*, Nature vol. 317, pp. 730-732 (1985).
M. Jochum, *Proteinases and their Inhibitors in Septicemia-Basic Concepts and Clinical Implications*, Adv. Exp. Med. Biol 167, 391-404 (1984).
P. Herion, *Monoclonal Antibodies Against Plasma Protease Inhibitors: Production and Characterization of 15 Monoclonal Antibodies Against Human Antithrombin III. Relation Between Antigenic Determinants and Functional Sites of Antithrombin III*, Blood vol. 65, pp. 1201-1207 (1985).
H. Lau, *The Isolation and Charcterization of a Specific Antibody Population Directed against the Thrombin Antithrombin Complex*, J. Biol. Chem., vol. 255(12); 5885-5893 (1980).
Fujisawa et al., Chem. Abstracts, 94(17):134816y (1981), *Latex Agglutination Method for the Measurement of Antithrombin III in Human Plasma*.
E. J. McKay, *Immunochemical Analysis of Active and Inactive Antithrombin III*, Brit J Hematol., 46:277-285 (1980).
Bick et al., *Antithrombin III (AT-III) as a Diagnostic Aid in Disseminated Intramuscular Coagulation*, Thrombosis Research, vol. 10 pp. 721-729 (1977).
Lau et al., *The Isolation and Characterization of a Specific Antibody Population Directed Against the Prothrombin Activation Fragments $F_2$ and $F_{1+2}$*, J. Biol. Chem., vol. 254 No. 18, pp. 8751-8761 (1979).

*Primary Examiner*—Esther L. Kepplinger
*Assistant Examiner*—Carol E. Bidwell
*Attorney, Agent, or Firm*—Elizabeth F. Enayati

[57] ABSTRACT

Indirect method of detecting elastase-modified or cleaved, antithrombin (ATx) in the presence of intact antithrombin (AT-III). The inventive method includes a modified ELISA using a detergent to alter the intact AT-III. Cleaved AT-III is generated in human plasma, then an ELISA is performed in the presence of a detergent.

2 Claims, 4 Drawing Sheets

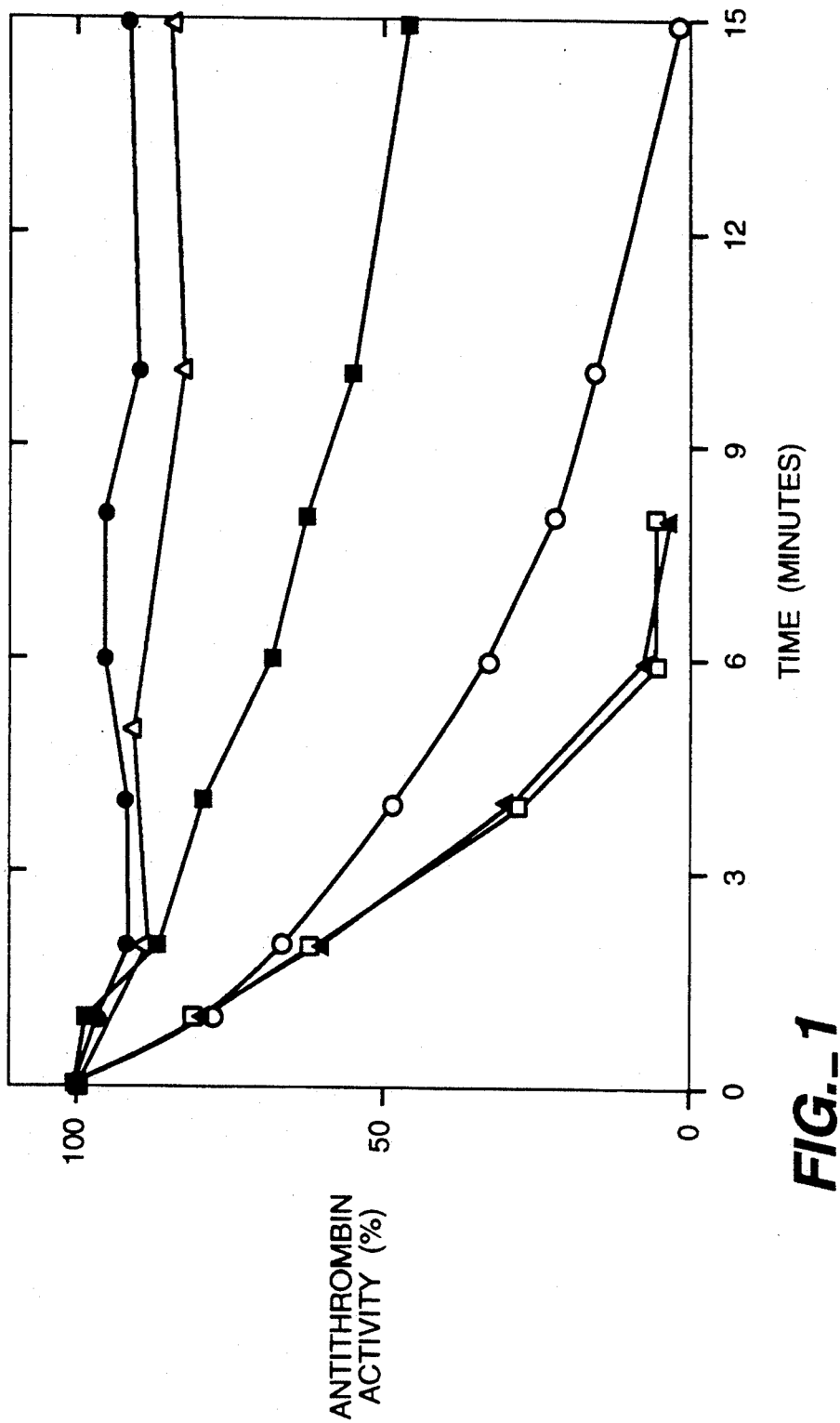
FIG._1

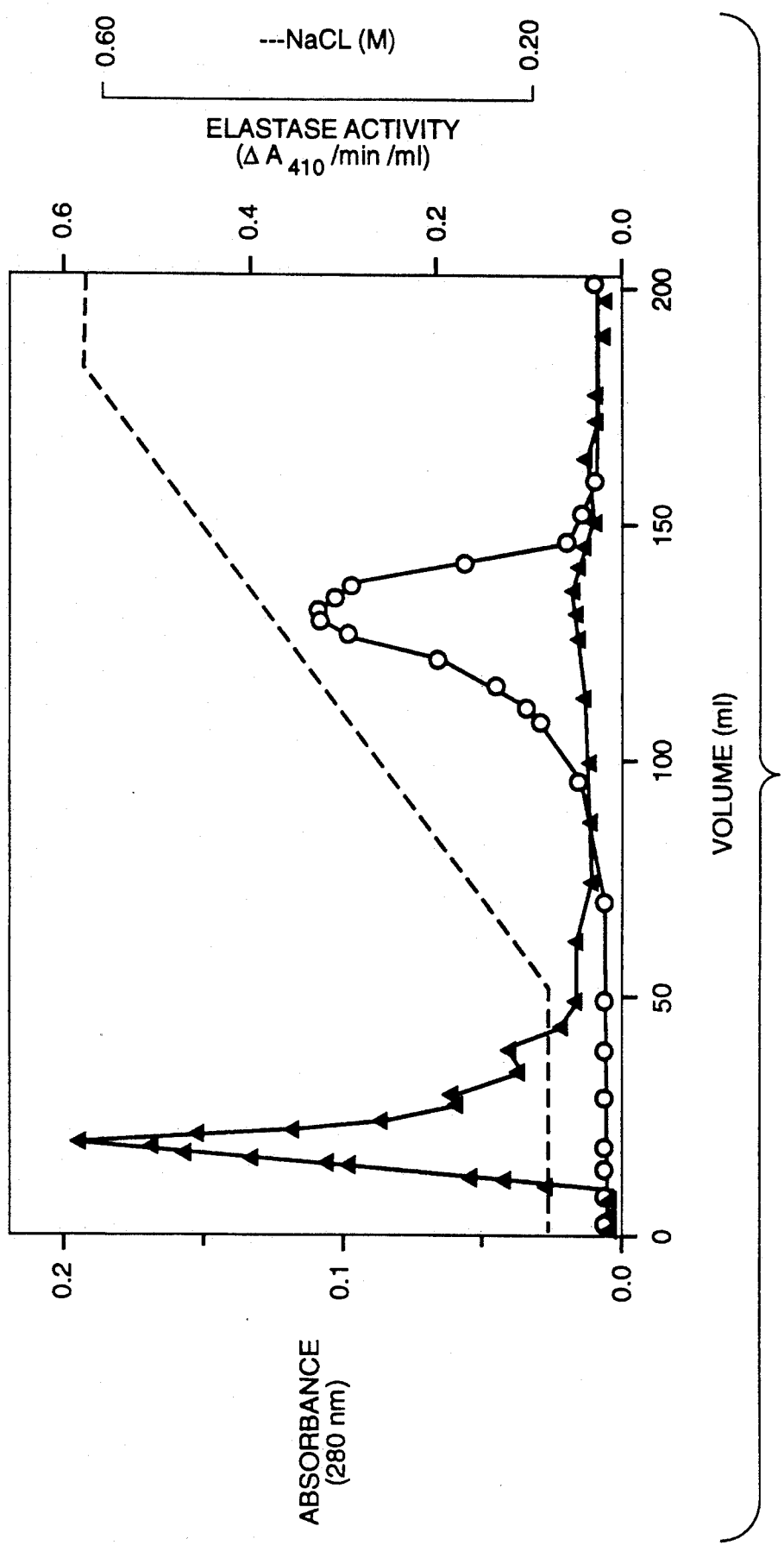
FIG._2

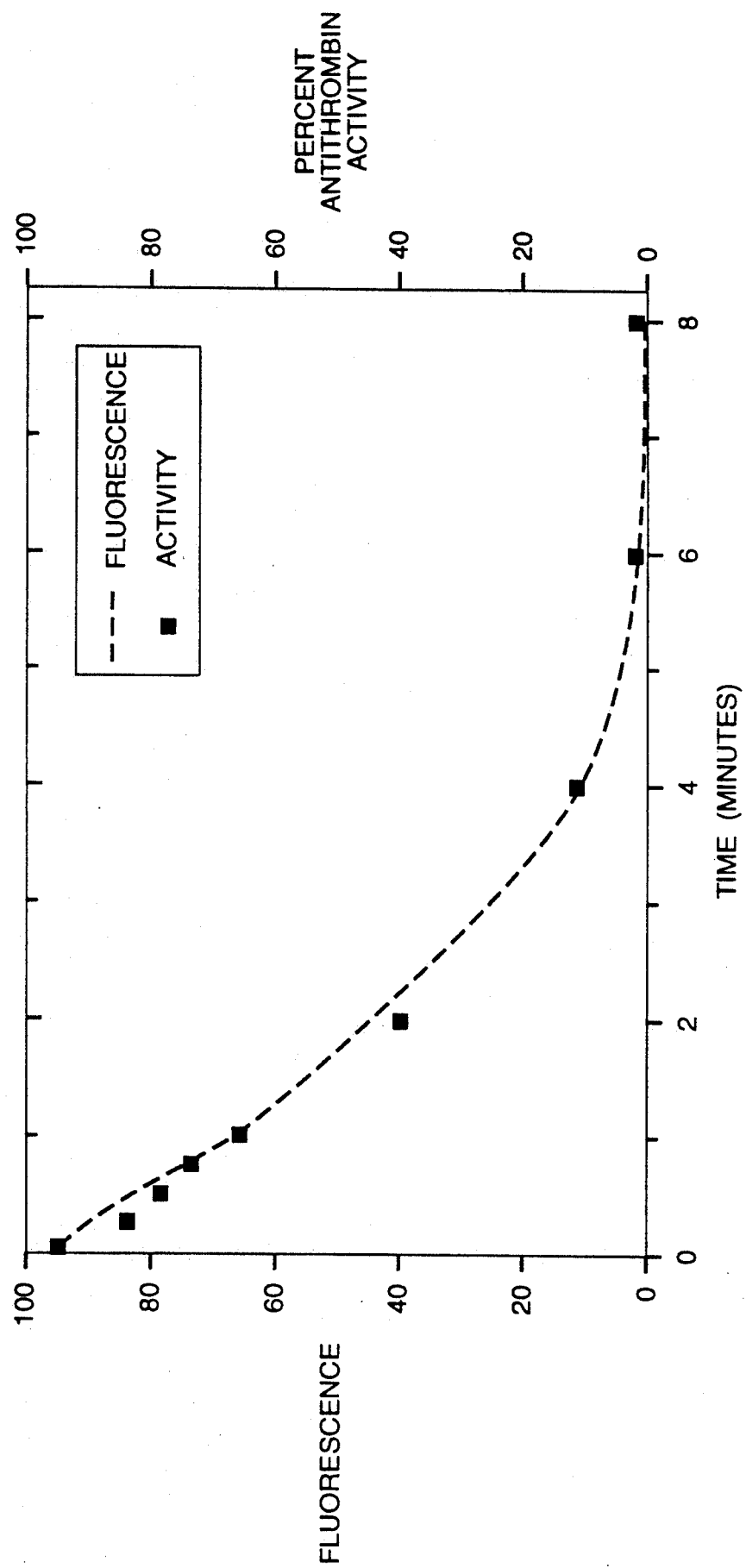
FIG._3

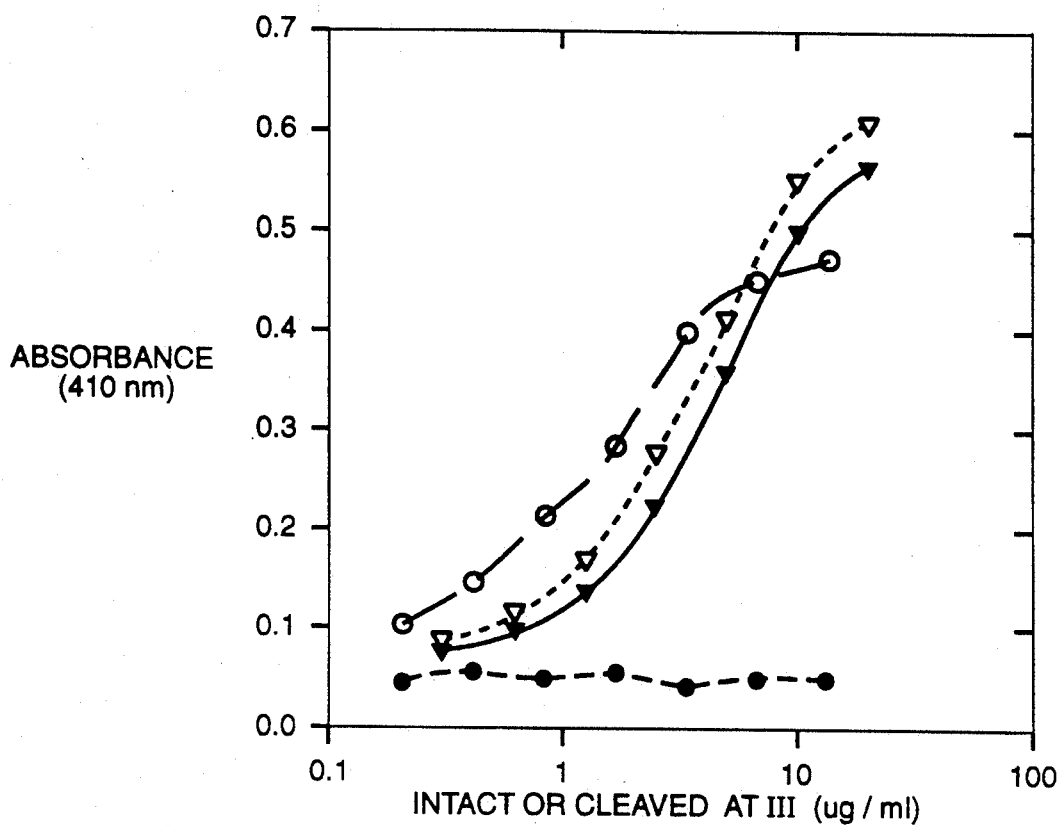
FIG._4
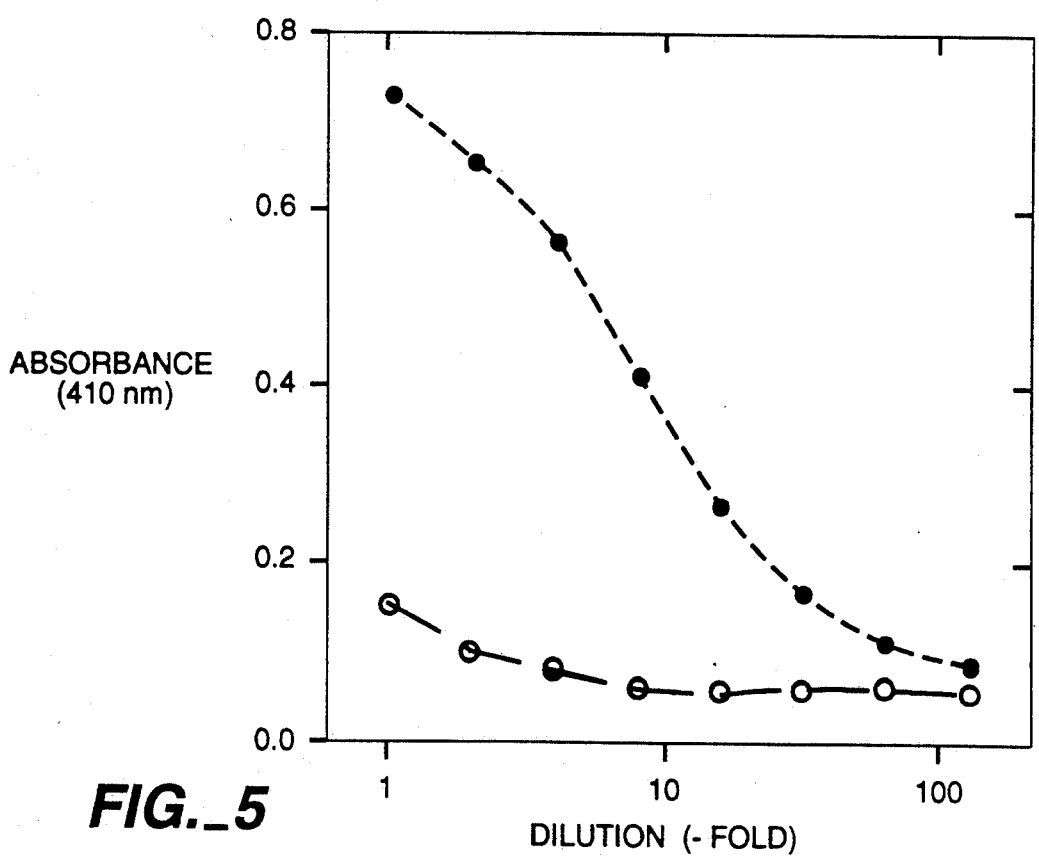
FIG._5

METHOD OF DETECTING PROTEOLYTICALLY MODIFIED ANTITHROMBIN

CROSS REFERENCE TO RELATED APPLICATIONS

This is a continuation-in-part of U.S. Ser. No. 07/381,547, filed Jul. 18, 1987 now abandoned, which is a continuation-in-part of abandoned U.S. Ser. No. 07/018,548, filed Feb. 25, 1987 now abandoned.

BACKGROUND OF THE INVENTION

The present invention relates to diagnostic assays, specifically an assay that detects a modified form of AT-III as a predictor of thrombotic and pre-thrombotic condition.

Antithrombin (AT-III), the primary plasma inhibitor of blood coagulation enzymes, is a member of a large superfamily of structurally related proteins which includes several serine proteinase inhibitors (serpins). These proteinase inhibitors share a common mechanism by which a covalent, essentially irreversible complex is formed with the target enzymes. During this process, the serpin is cleaved by the protease at the reactive center, allowing the inhibitor to change from its normal strained conformation to a relaxed conformation and resulting in the inactivation of the inhibitor. Several studies have shown that proteases can cleave serpins near their reactive center in such a way that the inhibitor is inactivated, but the protease is not.

It is possible to perform an evaluation of this sort of inactivation in vitro using purified components, but determination of its relevance in vivo where a large excess of active inhibitor exists is more difficult. Another possible approach would be to generate monoclonal antibodies specific for the cleaved form of the inhibitor and use them in an ELISA format. Although this method can work well, it is time consuming and relatively expensive.

Interestingly, several of these serine protease inhibitors are themselves the target of attack by proteinases of mammalian and non-mammalian origin. In the case of AT-III a specific and inactivating cleavage is known in vitro to be catalyzed by human neutrophil elastase (HNE) in a heparin-dependent fashion near the active site of the sequence of the inhibitor without any apparent effect in HNE activity. HNE is secreted by neutrophils during inflammation and may affect functional AT-III levels in vivo. This may contribute to the development of life-threatening thrombosis accompanying widespread activation of neutrophils in inflammation and septicemia.

Maintenance of plasma concentrations of AT-III at or near its normal level of approximately 2 micromolar is apparently essential to avoid a tendency toward blood clotting in both hereditary deficiency and disease. Disease related decreases, which can be more than 50% in extreme cases of septicemia, have often been attributed to the consumption of AT-III in the course of inhibiting coagulation enzymes.

The recently described in vitro inactivation of AT-III by neutrophil elastase (Jochum et al., Z. Physiol. Chem. 362:103, 1981) suggests a possible alternative explanation. Nevertheless, the extrapolation of this observation to the physiologic setting must take into account the very high plasma levels of a specific elastase inhibitor. This inhibitor, alpha-1 proteinase inhibitor, normally prevents expression of elastolytic activity in plasma.

The treatment of acquired antithrombin (AT-III) deficiencies, such as disseminated intravascular coagulation (DIC), septicemia and other inflammatory diseases, has been thwarted by the inability to diagnose the early onset of a pre-thrombotic state. Treatment of acquired deficiencies with AT-III or other elastase inhibitors has been delayed until clinical symptoms manifest themselves. Delayed treatment has had equivocal results. These equivocal results are thought to reflect the unpredictable severity and rate of onset of the disease state, as well as the likelihood of inadequate treatment doses.

Currently, determinations of functional plasma antithrombin constitute the only diagnostic test for ascertaining AT-III consumption or turnover during pathologic states. While these may give some information during or after major thrombotic episodes, they are insensitive to the prethrombotic condition. The consumption of AT-III in a limited or localized reactive zone, i.e., the formation of a clot on the vascular lining, would generally have little effect on the total plasma pool of antithrombin. Localized events within the vasculature, even when locally severe, have little impact on overall AT-III levels which are normally high (2 micromolar). The current clinical tests measuring AT-III levels are inadequate to diagnose potentially small changes occurring in pre-thrombotic conditions.

The anticoagulant heparin is a functionally heterogeneous sulfated carbohydrate with the ability to bind to AT-III and accelerate its rate of inhibition of coagulation enzymes. Heparin does not normally circulate in blood but, rather, is an integral component of vascular endothelial cell walls.

The anticoagulant activity of heparin, as purified from animal tissues and administered therapeutically, derives from a limited subfraction of heparin molecules (35%) possessing affinity for antithrombin.

Jochum et al., Eur. Surg. Res., 13:152–168 (1981) disclose that a protease inhibitor, aprotinin, may prevent the decline in plasma proteins in dogs made endotoxemic by infusion of E. coli endotoxin. Aprotinin may therefore be a candidate for treatment of DIC.

Jochum et al., Hoppe-Seyler's Z. Physiol. Chem. Bd., 362, S.: 103–112 (1981) disclose that granulocytic (neutrophil) elastase cleaves AT-III in vitro to produce a modified AT-III, and that some of the AT-III consumption in septicemia or endotoxemia may be due to proteolysis of AT-III.

Carrell et al., Nature, 317:730–732 (1985) further describe the conformational change brought about by elastase cleavage of AT-III.

Jochum et al., Adv. Exp. Med. Biol., 167:391–404 (1984) describe a study of AT-III, alpha-1-PI and other protein levels in septic patients. They found a significant decrease of AT-III activity in septic patients, presumably as a result of AT-III depletion of elastase released by neutrophils as part of the inflammatory response.

Biologically active AT-III has been expressed in E. coli transfected with human cDNA, as disclosed in Bock et al. U.S. Pat. No. 4,632,981.

Herion et al., Blood, 65(5):1201-7 (1985) describe monoclonal antibodies to AT-III.

Lau et al., J. Biol. Chem., 254(18):8751–8761 (1979) disclose making and using polyclonal antibodies directed to identified fragments of prothrombin.

Other immunoassays for AT-III are described in the literature. Fujisawa et al. describe a latex agglutination assay used to measure AT-III levels in healthy persons and patients with DIC; the results were comparable with a radial immunodiffusion assay (Chem. Abstr., 94:13481, 1981).

E. McKay, Brit. J. Hemat., 46:277-285 (1980), describes an electroimmunoassay for AT-III. One antiserum used differentiated active AT-III from AT-III-protease complexes. Anomalies incurred with previous AT-III assays are described.

Bick et al , Throm. Res., 10:721-729 (1977) describe an assay for AT-III which was used to monitor AT-III levels in DIC patients.

However, none of these prior art assays measure elastase modified (inactivated) AT-III (ATx). The measurement of AT-III is insensitive with regard to potential thrombotic states in that normal AT-III levels are much higher than needed for normal physiological coagulation balance. A substantial imbalance resulting in significant generation of ATx would only result in a slight (e.g. 5%) decrease in AT-III levels.

Normal individuals, however, possess no ATx. Detection of ATx suggests a pathological state. In addition, measurement of AT-III-protease complexes is hindered by the short circulation half-life of these complexes, on the order of 10 minutes. ATx, however, has a half life in the order of that of AT-III.

Detecting and measuring circulating elastase modified antithrombin (ATx), based on this mechanism, provides for early diagnosis and hence, treatment of the pre-thrombotic and thrombotic conditions. Thus, there remains a need for a reliable, efficient method of detecting ATx in serum samples.

SUMMARY OF THE INVENTION

This invention relates to diagnostic assays for detecting elastase-modified antithrombin. Elastase-modified (inactivated) AT-III is designated herein as ATx. ATx is homologous in primary structure to AT-III, but it does not function to inhibit thrombin or bind heparin because of a clip in the protein backbone which normally holds AT-III in its active configuration. Thus AT-III is conformationally different from ATx, and this difference may be exploited immunologically to develop specific diagnostic assays that detect ATx but not AT-III.

High circulating levels of ATx are diagnostic of a prethrombotic state, since normal turnover of AT-III does not result in production of ATx. Once a diagnosis is made, anticoagulant, fibrinolytic, or anti-elastase therapy can be instituted. An alternative therapy would include a recombinant antithrombin, not subject to elastase inactivation.

Direct means of detecting elastase-modified antithrombin may include using polyclonal antibodies, monospecific to the elastase modified antithrombin or monoclonal antibodies specific to the ATx.

Indirect methods of detecting ATx in the presence of AT-III include a modified ELISA using a detergent to alter the intact AT-III. Thus, proteolytically inactivated AT-III can be measured in the presence of intact AT-III by generating cleaved AT-III in human plasma, then performing an ELISA in the presence of a detergent.

BRIEF DESCRIPTION OF THE DRAWINGS

FIG. 1 is a graph showing the negligible rate of inactivation of antithrombin in the absence of heparin.

FIG. 2 is a graph showing the inability of elastase modified antithrombin (ATx) to bind to heparin.

FIG. 3 is a graph comparing the activity loss and fluorescence decay during human neutrophil elastase inactivation of AT-III.

FIG. 4 is a graph showing that SDS does not reduce HNE-cleaved AT-III reactivity in the AT-III ELISA. Intact (circles) or HNE-cleaved AT-III (triangles) are subjected to the cleaved AT-III ELISA with (solid symbols) or without (open symbols) SDS added. Values reported are absorbance units generated by a given concentration of AT-III.

FIG. 5 is a graph showing a dose response curve of HNE-cleaved AT-III spiked into assayed reference plasma.

DETAILED DESCRIPTION OF THE PREFERRED EMBODIMENT

Antithrombin III (AT-III) is a serine protease inhibitor (serpin) that can be catalytically inactivated by human neutrophil elastase (HNE) without inhibiting HNE activity. As with catalytic inactivation of most serpins, the cleaved form of the inhibitor is difficult to measure in the presence of active inhibitor. One major difference between the cleaved and intact forms of AT-III is that the cleaved form adopts a more stable conformation. The present invention involves an SDS-modified ELISA capable of detecting cleaved AT-III (i.e., ATx) in the presence of intact AT-III.

It seems likely that the SDS alters the intact AT-III so that it is not detected in the ELISA. As little as 5 ug/mL HNE-cleaved AT-III may be detected when spiked into human plasma. The inventive cleaved AT-III ELISA method may be used to measure proteolytically inactivated AT-III in the presence of intact AT-III and may be useful for studying the role of proteolytic inactivation of serpins such as AT-III in vivo.

Serine protease inhibitors (serpins) play important roles in regulating proteases involved in coagulation and inflammation. Serpin depletion via consumption or inactivation can have a dramatic effect on the control of many physiologic processes. Serpin inactivation can occur in vivo via proteolytic cleavage and could be a means of serpin inactivation in vivo. Serpins cleaved near the active center attain a more stable conformation.

The present inventive method involves an SDS-modified ELISA capable of detecting cleaved AT-III in the presence of excess intact AT-III. This assay uses the detergent SDS generally commercially available from Sigma Chemical, St. Louis, Mo. to eliminate the signal normally generated in a standard ELISA by intact AT-III.

In one form of the inventive method, the cleaved AT-III ELISA is a sandwich ELISA utilizing a rabbit anti-human AT-III polyclonal antibody for capture and a mouse anti-human monoclonal antibody with a goat anti-mouse polyclonal antibody conjugated to horse radish peroxidase for detection. The sample to be assayed is then incubated with SDS prior to testing the ELISA. SDS treatment generally causes a dramatic decrease in the ELISA signal for intact AT-III, but hardly any change occurs in the ELISA signal for cleaved AT-III. Comparable results may be seen when intact AT-III is present in human plasma. When cleaved AT-III is spiked into human plasma at different concentrations, the expected level of cleaved AT-III may be recovered. The cleaved AT-III ELISA may be used to measure proteolytically cleaved AT-III in human plasma.

Addition of SDS to the AT-III ELISA reduces reactivity of intact AT-III, but does not diminish the signal for cleaved AT-III. This cleaved AT-III ELISA then may be used to measure HNE- or thrombin-cleaved AT-III in human plasma. The inventive assay is sensitive and does not require generation of antibody specific for epitopes found on cleaved AT-III. It may be used for in vitro characterization of AT-III proteolytic cleavage and it may provide a means for monitoring generation of cleaved AT-III in vivo. The assay also may be used to measure cleaved AT-III generated in situ.

The specificity of the assay of the present invention for cleaved AT-III may be due to the enhanced stability of this serpin when it is in its cleaved (relaxed) conformation instead of its intact (strained) conformation, as demonstrated by the fact that thrombin-cleaved AT-III generates a signal comparable to HNE-cleaved AT-III. In addition, substitution of the monoclonal detecting antibody with a polyclonal antibody to AT-III raised in goats gives comparable differences in signal between cleaved and intact AT-III when SDS is added.

Under normal conditions, endothelial bound heparin forms a complex with AT-III to provide a vascular lining with a nonthrombogenic nature. Under certain conditions such as DIC, inflammation, and septicemia, the non-thrombogenic nature of the vascular lining is compromised resulting in life-threatening thrombosis. Recent studies have revealed that heparin has an affinity for neutrophil elastase which serves to subvert the normal anticoagulant function of heparin.

Heparin is an acceleratory co-factor for AT-III a circulating inhibitor of coagulation enzymes. The presence of this anticoagulant on blood vessel walls contributes to the nonthrombogenic properties of that surface. In apparent opposition to this function, heparin was found to greatly accelerate the inactivation of AT-III by neutrophil elastase. Inactivation rates were potentiated several hundred-fold in vitro by heparin fractions possessing anticoagulant activity. Neutrophil elastase also demonstrated considerable affinity for immobilized heparin. These results suggest a mechanism which, if operating in vivo, could lead to a localized neutralization of heparin function.

A study of the kinetics of the inactivation of highly purified human antithrombin by neutrophil elastase is presented in FIG. 1. For these in vitro studies, we found it to be essential to employ extremely well-characterized and highly purified antithrombin preparations. This is because heparin, and often platelet factor 4, a heparin neutralizing component, are frequent contaminants of antithrombin purified by affinity chromatography on immobilized heparin supports.

The absence of these contaminants may be insured by inclusion of specific separation steps and confirmed by specific assays of these components generally available to those skilled in the art. Human antithrombin was isolated by previously described techniques using heparin agarose affinity chromatography (Miller-Andersson, et al., Thromb. Res. 5: 439, 1974). Re-purification on heparin-agarose employing sodium chloride gradient elution (0.4–1.5M) served to separate antithrombin from the tighter binding platelet factor 4 (Jordan, et al., J. Biol. Chem. 257: 400, 1982). Residual contaminating heparin, deriving from the heparin affinity matrix, was removed by two passes over QAE-Sepharose (commercially available from Pharmacia Piscatoway, N.J.

Functional activity levels of heparin were assayed by a chromogenic substrate assay employing Factor Xa as described by Teien et al., Thromb. Res. 10: 399 (1977). Platelet Factor 4 levels were determined using a commercially available competitive radioimmunoassay kit (Abbott Laboratories, Chicago, Ill.).

The invention is further described in the following nonlimiting examples.

EXEMPLIFICATION

Example 1

Human neutrophil elastase was a gift of Dr. James Travis or was a human sputum- derived preparation obtained commercially from Elastin Products Co. (Pacific, Mo.).

A reaction mixture containing purified human antithrombin at a concentration of 2 micromolar and varying concentrations of heparin in 0.15M NaCl, 0.02M Tris-HCl, pH 7.5, was warmed to 37° C. Elastase was added to a concentration of 5 nanomolar to initiate the reaction. Reactions were stopped at the indicated times by a 20-fold dilution of an aliquot of the reaction mixture into the second-phase assay buffer (0.15M NaCl, 0.05M Tris-HCl, pH 8.4) containing 1 microgram per milliliter of alpha-1 proteinase inhibitor. Antithrombin activity was then determined by a chromogenic substrate heparin cofactor assay as described in Rosenberg, et al., Reviews of Hematology, Vol. II (G. Murano, ed., 1986).

In the present example, the individual reaction mixtures were as follows: no added heparin (•); 1 microgram/ml inactive heparin (Δ); 50 (■), 100 (0), 400 (▲) or 700 (□) nanograms per ml of the anticoagulantly active heparin species. These legends are used in FIGS. 1 and 2.

As shown in FIG. 1, inactivation of antithrombin occurred at a negligible rate in the absence of heparin. When small amounts of anticoagulantly active heparin were included, however, a progressive and eventually complete loss of the inhibitory activity of antithrombin occurred. In the curve representing a heparin concentration of 50 ng/ml, the approximate calculated molar ratios of heparin, elastase and antithrombin were 1/1.5/600, respectively. Rates of inactivation were dependent on heparin concentrations at low levels but reached an apparent maximum velocity at approximately 0.5 µg/ml of the active heparin species. Thus, to achieve maximum inactivation rates, a heparin concentration less than 2% of that required for stoichiometric equivalence with antithrombin was needed.

These studies indicate that both heparin and elastase act catalytically to inactivate antithrombin. This catalytic role for elastase distinguishes the mechanism of the present inactivation phenomenon from the inhibition of clotting enzymes by antithrombin. In the latter case, heparin catalyzes the formation of a covalent, stoichiometric complex between antithrombin and enzyme.

To determine the magnitude of the present heparin effect, we compared the rate of inactivation of the presence or absence of a saturating level of heparin (10 µg/ml) and assumed that first order kinetics were obeyed in each case. Employing 5 nM elastase and 500 nM antithrombin, an approximately 400-fold rate enhancement was observed. This enhancement value derives from the ratio of velocities of 650 nM/min in the presence and 1.6 nM/min in the absence of the active heparin species. Although the determination of this rate enhancement reflected a quite arbitrary set of conditions and reactant concentrations, its magnitude emphasizes that heparin can greatly accelerate this inactivation phenomenon.

FIG. 1 also shows that the inactive heparin fraction failed to promote the cleavage of antithrombin by elastase.

Other glycosaminoglycans including dermatan sulfate, chondroitin 4-sulfate, chondroitin 6-sulfate, and dextran sulfate were also without significant stimulatory effect at a similar concentration (data not shown). The distinguishing characteristic of active heparin, in contrast to the inactive heparin fraction and other sulfated carbohydrates, is its ability to bind with high affinity and specificity to antithrombin. The apparently stringent requirement for the active heparin species in the present reaction strongly suggests that a heparin-antithrombin complex is the substrate for elastase attack.

A profound heparin-dependency was observed for the in vitro inactivation of purified human antithrombin by neutrophil elastase. In the absence of heparin, or when heparin-blocking agents such as platelet factor 4 or polybrene were present during the incubation, little or no antithrombin inactivation occurred. Only catalytic amounts of heparin were required to cause the complete inactivation of antithrombin enzyme: inhibitor ratios of 1:400 in 5–10 minutes. The elastase-cleaved form of antithrombin loses affinity for heparin as a result of a limited cleavage at a site approximately 42 amino acids from the carboxyterminus. We isolated this inactive antithrombin species and injected it into rabbits for determination of its circulating half-life. Interestingly, elastase-inactivated antithrombin remains in circulation for a prolonged period (T1/2~13hrs) in comparison to thrombin-antithrombin complexes (T½ is less than 10 min.) and may provide a better explanation for the circulating, non-functional antithrombin and suggests a mechanism by which, during inflammatory conditions, the usually non-thrombogenic nature of the vascular lining may be neutralized.

The rate of inactivation of inhibition of coagulation enzymes by AT-III is greatly increased by an interaction between the inhibitor and a limited, anticoagulantly-active subfraction of heparin molecules. We have observed that this same heparin sub-fraction also greatly stimulates the rate of inactivation of antithrombin by neutrophil elastase. Inactivation rates were increased several hundred-fold by catalytic amounts of the anticoagulantly active heparin species and were unaffected by the inactive heparin fraction or other glycosaminoglycans.

Preliminary kinetic analysis using the elastase-catalyzed reversal of the heparin-induced increase in antithrombin fluorescence suggested a Km of less than 1 $\mu$M for the heparin-antithrombin complex substrate and a turnover of several hundred per minute per enzyme molecule. Although the specificity of the heparin effect appears to be at the level of its interaction with antithrombin, an elastase-heparin interaction could also be detected in kinetic analyses.

Chromatographic studies employing immobilized heparin confirmed that elastase itself binds tightly to the carbohydrate whereas the elastase-cleaved form of antithrombin shows no affinity for heparin. These results suggest a complex and potentially physiologically-relevant mechanism in which both heparin and elastase act catalytically to direct the inactivation of antithrombin. Since anticoagulantly-active heparin species are present on endothelial cells, the above mechanism could markedly affect the balance between procoagulant and anticoagulant events on the usually non-thrombogenic endothelial surface.

FIG. 2 shows the heparin-Sepharose chromatography of elastase-inactivated antithrombin. A reaction mixture containing 5 mg of antithrombin and 150 $\mu$g of elastase was initiated with a trace amount of heparin and monitored for antithrombin functional activity until inactivation was complete. Before application of the reaction mixture on the column, free heparin was removed by adsorption on QAE-Sepharose. The reaction mixture was applied to a pre-equilibrated heparin-Sepharose column (1.1×8.8 cm) in a buffer consisting of 0.25M NaCl, 0.02M Tris-HCl, pH 7.5. Elastase-inactivated antithrombin (▲) eluted as a single unbound peak under the conditions of application. Elastase was eluted by a 120 milliliter linear gradient of NaCl from 0.25 to 0.6M. Elastase activity (○) was detected by its ability to hydrolyze the chromogenic substrate methoxysuccinyl-ala-ala-pro-val-paranitroanalide (Sigma) as described in Nakajima et al., 254 J. Biol. Chem 4027 (1979). The activity contained in each column fraction was normalized to the amount of absorbance generated at 410 nm in one minute per mil of column eluate.

In the course of the present investigations, we also observed a tight binding interaction between heparin and neutrophil elastase itself. The major peak of elastase activity eluted at a sodium chloride concentration of approximately 0.5M. No elastase activity was detected in the unabsorbed eluate region containing the elastase-cleaved antithrombin. The avidity of the enzyme for heparin was only slightly less than that of functionally active antithrombin itself under similar conditions of chromatography.

This binding interaction between the highly cationic elastase and the acidic affinity matrix may be primarily electrostatic in nature. Neutrophil elastase has been previously purified on the basis of its affinity for chromatography gels containing sulfonate residues. Surprisingly, a similar interaction with the physiologically relevant sulfated carbohydrate, heparin, has not been previously reported.

The consequence of heparin/neutrophil elastase interactions on the kinetics of antithrombin inactivation are uncertain. While these two components act together as catalysts to inactivate antithrombin, the data of the present study would not suggest any mutual specificity between them. Rather, the inactivation of antithrombin occurs only in the presence of the anticoagulantly active heparin fraction which binds specifically to antithrombin. Moreover, this latter association is apparently tighter than that between heparin and elastase. Notwithstanding these considerations, an interaction between elastase and endothelial-bound heparin in vivo might localize the enzyme and sequester it from plasma inhibitors while simultaneously bringing it into close approximation with antithrombin molecules bound at that surface. Viewed from this perspective, the affinity of neutrophil elastase for heparin may thus have a profound effect on the kinetics of antithrombin inactivation and may be an essential component of the mechanism.

The inhibition of coagulation enzymes by the antithrombin-heparin system is accepted as a crucial regulatory mechanism of the clotting process. The recent demonstration of anticoagulantly active heparin on the vascular endothelium (Stern et al., J. Clin. Invest. 79:272, 1985; Marcum et al., J. Biol. Chem., 261:7507, 1986) identifies the antithrombin/heparin system as an important component in the balance between procoagulant and anticoagulant pathways. The results of the present in vitro study suggest, however, that under certain conditions, the binding of antithrombin by heparin may lead to a quite different outcome. The rapid and specific inactivation of heparin-bound antithrombin by elastase represents a novel and unexpected function for heparin. A similar occurrence on in vivo heparin sites could result in a localized reversal of the non-thrombogenic character of the vascular lining.

In contrast to current methods of determination of functional plasma antithrombin levels, the detection of elastase modified antithrombin (ATx) would provide a sensitive probe for detection of pre-thrombotic conditions. Suitable diagnostic probes for detecting elastase modified antithrombin are directed to the structural or conformational differences between antithrombin and elastase modified antithrombin. The elastase-modified antithrombin (ATx) is in a different conformation because the neutrophil elastase has clipped or cleaved the approximately 58,000 dalton molecule at a site approximately 42 amino acids from the carboxy terminus.

The presence or absence of elastase modified antithrombin can be detected directly or indirectly. A direct means for detecting elastase modified antithrombin is to determine its presence using polyclonal antibodies, monospecific to the elastase modified antithrombin. The polyclonal antibodies can be obtained by injecting a host with elastase modified antithrombin, allowing the host to produce polyclonal antibodies to said elastase modified antithrombin and recovering the polyclonal antibodies from the host. Booster injections of elastase modified antithrombin can be used to increase the yield of polyclonal antibodies. Polyclonal antibodies that cross-react with antithrombin and elastase modified antithrombin are removed. Polyclonal antibodies that are monospecific to the elastase modified antithrombin are then used by reacting said polyclonal antibodies, with a sample suspected of containing elastase modified antithrombin and determining the quantity or presence of monospecific polyclonal antibodies bound to the antigen.

A second direct means of detecting elastase modified antithrombin is to provide a monoclonal antibody, specific to said elastase modified antithrombin to measure the presence or absence of elastase modified antithrombin. Monoclonal antibodies can be derived from hybridomas selected from appropriate fusion partners so that monoclonal antibodies, specific to elastase modified antithrombin are expressed. Methods of obtaining hybridomas include: Polyethylene glycol (PEG) mediated fusion of murine myeloma cells of BALB/c or other origin such as P3-X63Ag8 and SP2/o-Ag14 or derivatives thereof with splenocytes from a BALB/c mouse immunized with elastase modified antithrombin; electrofusion of murine myeloma cells and splenocytes as listed above; PEG mediated or electrofusion of non-BALB/c myeloma with non-BALB/c splenocytes from an elastase modified antithrombin immunized mouse; or electrofusion or PEG mediated fusion of murine myeloma cells as listed above with splenocytes immunized in vitro for 3-6 days following either no in vivo immunization or a primary in vivo immunization with elastase modified antithrombin. It is within the scope of this invention that more than one monoclonal antibody specific to different epitopes may be used to detect the presence or absence of elastase modified antithrombin. The monoclonal antibodies would be reacted with a sample suspected of having elastase modified antithrombin, and the presence or quantity of monoclonal antibodies bound to antigen determined.

An indirect means for detecting the presence or absence of elastase modified antithrombin would be to separate or purify the smaller polypeptide from the larger polypeptide. Initial studies reveal that the smaller polypeptide includes an approximately 42 amino acid sequence; the larger polypeptide includes an approximately 390 amino acid sequence. The smaller polypeptide can be separated by the reduction of the linking disulfide bond followed by separation of the larger polypeptide using techniques such as selective precipitation, chromatography or electrophoresis. Detection of the smaller separated polypeptide can be done by polyclonal or monoclonal antibody methodologies or by more conventional chemical techniques such as fluorometric, colorometric or radiolabelling methodologies.

The above immunochemical assay systems could be performed using well known techniques such as radioimmunoassay (RIA), dot blots or Western blotting.

The above diagnostic probes can be used for diagnosis of a pre-thrombotic state and for monitoring the effectiveness of anticoagulant, anti-elastase, fibrinolytic or recombinant antithrombin (not subject to elastase inactivation) therapy. A first sample prior to the initiation of therapy would be reacted with a diagnostic probe and the amount of elastase modified antithrombin measured. Following the initiation of therapy, one or more samples could be measured. A comparison between the pre and post treatment samples could be made, with a decrease in the level of elastase modified antithrombin indicating the effectiveness of the therapy. The level of elastase modified antithrombin could be measured at a plurality of intervals and following a plurality of treatment doses.

A recombinant antithrombin not subject to elastase inactivation would provide an alternative therapy. Such a recombinant antithrombin would lack the elastase cleavage site found in naturally occurring antithrombin.

It was observed that neutrophil elastase reverses the heparin-induced enhancement of antithrombin fluorescence. As shown in FIG. 3, the rate of conversion of antithrombin to elastase modified antithrombin can be demonstrated as a function of time. A $1 \times 10^{-6}$M sample of antithrombin was run on the spectroflurometer, as was a sample containing $1 \times 10^{-6}$M antithrombin and $1 \times 10^{-5}$M heparin to show the heparin-induced enhancement of antithrombin. Neutrophil elastase was added to the sample in a concentration of $5 \times 10^{-9}$M. Analysis at 10 minutes demonstrates the reversal of the heparin-induced enhancement. The rate of conversion can be determined as a function of time by setting the spectrometer at 330 nanometers and run the sample as soon as the elastase is added. All of the samples were excited at 280 nanometers and emission was read at 330 nanometers.

EXAMPLE 2

The following materials are used in this example: Maxisorp F97 Immunoplates from Nunc [Newbury Park, Calif.]; human neutrophil elastase was from Elastin Products Pacific, Mo.; rabbit antihuman AT-III polyclonal antibody, bovine albumin and ABTS (2, 2'-azinobis 3-ethylbenzyl-thiazoline-6-sulfonic acid) are from Sigma Chemical (St. Louis, Mo.); goat anti-mouse antibody conjugated to horse radish peroxidase are from Biorad Richmond, Calif.; mouse anti-human AT-III monoclonal antibody are from Interferon Sciences, New Brunswick, N.J.; assayed reference plasma are from Helena Labs Beaumont, Tex.; remaining chemicals are of reagent grade. AT-III and HNE-cleaved AT-III are prepared by methods generally publicly available (see, Jordan et al., 264 J. Biol. Chem. 10493, 1989).

Plates are coated overnight by rocking at 4' C. with 50 μL of 4 μg/mL rabbit anti-AT-III polyclonal antibody in 50 mM carbonate, pH 9.6. Plates are then washed three times with PBS containing 0.05% Tween 20 using a Skatron plate washer. All subsequent incubations are performed for 1 hour at room temperature with rocking. Plates are blocked with 250 μL 5% non-fat dry milk in 0.1M Tris, pH 7.8, 0.5M NaCl and washed 5 times with PBS containing 0.05% Tween 20. Samples are then prepared by adding 5 μL sample to 40 μL diluting buffer (0.1% BSA, 0.1M Tris, pH 7.8, 0.5M NaCl), plus 5 μL 10% SDS and then incubating 5 minutes at room temperature. Diluting buffer (200 μL) is then added and 50 μL of this preparation placed in Row A of a microtiter plate. Subsequent 2-fold dilutions of this preparation are made with diluting buffer in rows B through H. Assayed reference plasma is used as a negative control while 40 μg/mL HNE-cleaved AT-III is used as a positive control. For the standard curve, 5 μL assayed reference plasma, 5 μL 40 μg/mL HNE-cleaved AT-III and 5 μL 10% SDS are added to 35 μL diluting buffer and processed as above.

Following incubation with sample, plates are washed 5 times as above and 100 μL of a 0.25 μg/mL anti-human AT-III monoclonal antibody in diluting buffer is added. Plates are incubated and washed as above, then 100 μL goat anti-mouse antibody conjugated to horse radish peroxidase (diluted 1:1000 in diluting buffer) is added. After washing as above, substrate (100 μL of a mixture containing 5 μL 30% hydrogen peroxide in 10 mL 0.5 mM ABTS, 0.1M citrate buffer, pH 4.8) is added and absorbance at 410 nm (450 nm reference) is determined using a Dynatech plate reader equipped with Titercalc software. Cleaved AT-III concentrations may be calculated using a Log-Logit transformation.

FIG. 4 is a graph showing that SDS does not reduce HNE-cleaved AT-III reactivity in the AT-III ELISA. Intact (circles) or HNE-cleaved AT-III (triangles) are subjected to the cleaved AT-III ELISA with (solid symbols) or without (open symbols) SDS added. Values reported are absorbance units generated by a given concentration of AT-III. As shown in that figure, addition of SDS to a sandwich ELISA system designed to detect AT-III resulted in a marked decrease in signal for intact AT-III, but has little effect on the signal generated by HNE-cleaved AT-III. This result suggests that SDS treatment be used to detect cleaved AT-III in the presence of intact AT-III, such as in patient plasma samples.

FIG. 5 is a graph showing a dose response curve of HNE-cleaved AT-III spiked into assayed reference plasma. HNE-cleaved AT-III is spiked into assayed reference plasma at a concentration of 40 μg/mL and subjected to the cleaved AT-III ELISA (solid circles). Absorbance values obtained following 2-fold dilution of sample are shown where points correspond to 40, 20, 10, 5, 2.5, 1.25, 0.63 and 0.32 μg/mL cleaved AT-III. For comparison, values obtained for unspiked plasma are also shown (open circles). Treatment of assayed reference plasma, containing approximately 125 μg/mL intact AT-III, with SDS reduces the AT-III ELISA signal to a low level (i.e. absorbance ≦0.2), while HNE-cleaved AT-III spiked into assayed reference plasma is still detected in the presence of SDS.

HNE- and thrombin-cleaved AT-III are spiked into normal plasma at varying concentrations and the apparent level of cleaved AT-III is determined by the cleaved AT-III ELISA. As little as 5 μg/mL cleaved AT-III spiked into normal plasma may be detected.

TABLE I

| Recovery of Cleaved AT-III Spiked into Normal Plasma | | |
| --- | --- | --- |
| Protease Used for Cleavage | Cleaved AT-III Added (μg/mL) | Cleaved AT-III Recovered (Mean ± SEM, μg/mL) |
| HNE | 0 | Not Detected |
| " | 5 | 5.9 ± 0.3 |
| " | 10 | 11.7 ± 1.3 |
| " | 20 | 20.5 ± 1.1 |
| " | 40 | 39.7 ± 1.4 |
| Thrombin | 40 | 46.7 ± 1.8 |

Values for cleaved AT-III recovered represent an average of at least 3 points. For AT-III cleaved by either protease, the amount of cleaved AT-III detected in the assay is comparable to that which was added. This suggests that the conformational change resulting from proteolytic cleavage, rather than the precise point of cleavage, renders cleaved AT-III stable to SDS treatment.

To evaluate whether the cleaved AT-III ELISA detects AT-III cleaved by HNE in situ in human plasma, HNE is incubated with normal plasma in the presence of increasing levels of heparin, then assayed using the cleaved AT-III ELISA. The results are shown in the following Table II.

TABLE II

| Heparin-Dependent Generation of Cleaved AT-III in Plasma by HNE | | |
| --- | --- | --- |
| Heparin Concentration (units/mL) | HNE (μM) | Cleaved AT-III (μg/mL) |
| 0 | 0 | Not Detected |
| 0 | 3.3 | " |
| 0.05 | 3.3 | " |
| 0.5 | 3.3 | 5 |
| 5 | 3.3 | 17 |
| 5 | 0 | Not Detected |

Heparin and HNE were added to normal plasma and incubated 15 minutes at 37° C. prior to assay. Plasma plus 5 units/mL heparin in the absence of HNE did not generate cleaved AT-III. Levels of heparin greater than 0.5 units/mL yields detectable levels of cleaved AT-III in the ELISA. No cleaved AT-III is detected in the absence of either HNE or heparin.

Given the above disclosure it is understood that variations will occur to those skilled in the art. Accordingly, the above examples are to be construed as illustrative and the scope of the invention disclosed herein is only to be limited by the following claims.

We claim:

1. A method of determining a pathological state of inactivation of antithrombin by human elastase by detecting the presence of elastase-modified antithrombin ATx in a patient, comprising the sequential steps of:
   A) obtaining a serum sample from said patient, said sample including intact antithrombin AT-III and elastase-modified antithrombin ATx;
   B) incubating said sample with a predetermined amount of sodium dodecyl sulfate detergent thereby forming a serum-detergent solution wherein said amount of said detergent is sufficient to conformationally alter AT-III without altering the conformation of ATx; and
   C) performing an ELISA to detect ATx in said solution formed in step B using a capture antibody and a detection antibody that each specifically bind intact AT-III and ATx but not conformationally altered AT-III formed in step B wherein the presence of ATx in said solution is an indication of said pathological state.

2. The method of claim 1 comprising the further step after Step (B) of diluting said serum detergent solution with a physiologically neutral rubber solution.

* * * * *